United States Patent [19]

Billings et al.

[11] 3,995,062

[45] *Nov. 30, 1976

[54] HALOCYCLOPROPYL HALOMETHYL ETHERS

[75] Inventors: Charles A. Billings, Concord; Gerald J. O'Neill, Arlington; Charles W. Simons, Bedford; Robert S. Holdsworth, Arlington, all of Mass.

[73] Assignee: W. R. Grace & Co., Cambridge, Mass.

[ * ] Notice: The portion of the term of this patent subsequent to Sept. 16, 1992, has been disclaimed.

[22] Filed: July 11, 1975

[21] Appl. No.: 595,285

Related U.S. Application Data

[62] Division of Ser. No. 536,411, Dec. 26, 1974, Pat. No. 3,932,529.

[52] U.S. Cl. .............................. 424/339; 260/611 R
[51] Int. Cl.² ....................................... A61K 31/075
[58] Field of Search ................. 424/339; 260/611 R

[56] References Cited
UNITED STATES PATENTS 3,906,111  9/1975  Billings et al. ...................... 424/339

Primary Examiner—Jerome D. Goldberg
Attorney, Agent, or Firm—Armand McMillan; C. E. Parker

[57] ABSTRACT

The following halocyclopropyl halomethyl ethers have been synthesized and found to possess utility as general inhalation anesthetics:

1-chloro-2-chlorofluoromethoxy-1,2,3,3-tetrafluorocyclopropane,
1-chloro-2-difluoromethoxy-1,2,3,3-tetrafluorocyclopropane,
1-bromo-2-chlorofluoromethoxy-1,2,3,3-tetrafluorocyclopropane and
1-bromo-2-difluoromethoxy-1,2,3,3-tetrafluorocyclopropane.

5 Claims, No Drawings

HALOCYCLOPROPYL HALOMETHYL ETHERS

RELATED APPLICATIONS

This application is a division of application Ser. No. 536,411 filed on Dec. 26, 1974 and now U.S. Pat. No. 3,932,529.

THE PRIOR ART

In the continuing search for general inhalation anesthetics, there has been recently discovered a few halocyclopropanes and methylhalocyclopropanes and some methylhalocyclopropyl ethers. These compounds are disclosed in U.S. Pat. Nos. 3,839,589 3,865,950 and 3,769,429 as well as in pending applications Ser. No. 499,761 (filed Aug. 22, 1974) for the methylcyclopropanes, and Ser. No. 451,677 (filed Mar. 15, 1974) for the methyl ethers. Prior to these current developments, which have been contributed to the art by the present applications, the only known cyclopropane compounds with a claim to anesthetic utility were cyclopropane itself and the 1-methyl-1-trifluoromethylcyclopropane reported by Krantz and Rudo [Handbuch of Experimental Pharmakologie 20 (1), at page 525 (1966)]. On assessing the progress reported in the art, as just reviewed, one must agree with these authors who, after an extensive compilation of the results of a few hundred tests on fluorinated compounds, conclude that cyclic halogenated compounds tend to be toxic. In fact, it has been the applicants' experience generally that for each useful compound discovered, there has been found one or more other structurally closely related compounds which are either useless or deleterious. Thus, despite the disclosures in recent years, it can be reasonably said that little has been added to the understanding of the mode of action of chemical compounds in this physiological role and, because of this, the relationship of the similarities and differences between fairly similar compounds with either their toxic or therapeutic properties remains substantially unidentified. The discovery of additional substances possessing a desirable combination of properties for anesthetic purposes still lies, therefore, beyond the scope of routine expertise.

SUMMARY OF THE INVENTION

It has now been discovered that the following newly synthesized compounds possess utility as general anesthetics when administered to inhalation-anesthetic-susceptible organisms: 1-chloro-2-chlorofluoromethoxy-1,2,3,3-tetrafluorocyclopropane, 1-chloro-2-difluoromethoxy-1,2,3,3-tetrafluorocyclopropane, 1-bromo-2-chlorofluoromethoxy-1,2,3,3-tetrafluorocyclopropane and 1-bromo-2-difluoromethoxy-1,2,3,3-tetrafluorocyclopropane.

DETAILED DESCRIPTION

The compounds of this invention were prepared from the corresponding halocyclopropyl methyl ethers by chlorination of the methoxy group followed by treatment with antimony trifluoride to replace the chlorine atoms by fluorine atoms. The preparation of the halocyclopropyl methyl ethers themselves is described in copending application Ser. No. 451,677 (filed on Mar. 15, 1974).

Specific preparations of the compounds of this invention are illustrated by the following examples. These examples are not limiting inasmuch as other ways can be devised by the men skilled in the art to prepare the same compounds such as for instance the direct cyclization of a suitable halocarbene with an appropriately substituted olefinic compound in the manner employed for the synthesis of the halocyclopropyl methyl ethers used in the method presently described.

EXAMPLE 1

1-Chloro-2-dichloromethoxytetrafluorocyclopropane

This compound may be prepared in a three-neck Pyrex flask equipped with a magnetic stirrer, a thermometer, a chlorine introduction tube and, in series, a cold-water reflux condenser, a −40° Dewar reflux condenser, a −40° trap and a water bubbler. The flask is placed in a water bath which is cooled by occasional addition of chips of dry ice.

Placed in the flask are 1.27 moles of 1-chloro-2-methoxy-1,2,3,3-tetrafluorocyclopropane. During irradiation of the flask by the light of a 275-watt sunlamp, 2.45 moles of chlorine are introduced into the stirred reaction mixture. The temperature of the mixture is maintained within the range of 15° to 35° C. In this manner, there has been obtained a 73.6% yield of 1-chloro-2-dichloromethoxytetrafluorocyclopropane based on the starting ether.

EXAMPLE 2

1-Chloro-2-difluoromethoxytetrafluorocyclopropane

This preparation can be carried out in a three-neck flask equipped with a heating mantle, a magnetic stirrer, a thermometer, an addition funnel and, in series, a reflux condenser, a −75° C trap and a nitrogen bubbler. The condenser is maintained at about 80° C with a constant temperature circulating bath. Added to the flask are 0.4 mole of $SbF_3$ and 7 g of $SbCl_5$. While heating the flask to 60° to 125° C, 0.4 mole of 1-chloro-2-dichloromethoxy-1,2,3,3-tetrafluorocyclopropane is added dropwise. The product is collected in the −75° trap. There has thus been obtained 1-chloro-2-difluoromethoxytetrafluorocyclopropane in 81% yield, based on the starting dichloromethoxy compound. The purified compound had a boiling point of 61.5° C, a density of ($d_4^{20}$) 1.573 and a refractive index of ($n_D^{20}$) 1.3144.

EXAMPLE 3

1-Chloro-2-chlorofluoromethoxytetrafluorocyclopropane

This compound may be prepared by the method of Example 2 no changes are actually required. The reactants used are $SbF_3$, 0.63 mole, $SbCl_5$, 0.037 moles, and 1-chloro-2-dichloromethoxy-1,2,3,3-tetrafluorocyclopropane, 0.61 mole. The condenser is kept at about 80° C and the reaction flask is heated at 70° to 148° C. Obtained in this manner is a yield of 5.6% of the chlorofluoromethoxy compound, based on the starting dichloromethoxy material. The purified product had a boiling point of 69° C, a density of ($d_4^{20}$) 1.588 and a refractive index of ($n_D^{20}$) 1.3276.

EXAMPLE 4

1-Bromo-2-dichloromethoxytetrafluorocyclopropane

This compound can be prepared by the method of Example 1, using, for instance, 0.054 mole of 1-bromo-2-methoxy-1,2,3,3-tetrafluorocyclopropane, and 0.1 mole of chlorine. A 72% yield, based on the 2-methoxy compound is thus obtained.

then calculated from these minimum concentrations. The results of these tests are summarized in the following table.

ANESTHETIC PROPERTIES OF HALOMETHYLCYCLOPROPYL ETHERS

| Ex. | 1,2,3,3-Tetrafluorocyclopropane | $AC_{50}$ (% volume) | $LC_{50}$ (% volume) | AI ($LC_{50}/AC_{50}$) |
|---|---|---|---|---|
| 7 | 1-Cl-2-diFmethoxy- | 2–10% | >10% | >1 |
| 8 | 1-Cl-2-ClFmethoxy- | 2% | 8–10% | 4–5 |
| 9 | 1-Br-2-diFmethoxy- | 1% | >4% | >4 |
| 10 | 1-Br-2-ClFmethoxy- | 2–4% | 6–8% | ~2 |

*When two figures are given, the actual parameter lies between them.

EXAMPLE 5

1-Bromo-2-difluoromethoxytetrafluorocyclopropane

This compound can be prepared in the manner of Example 2, but with the following changes. The condenser is kept at about 95° C and the reaction container heated at 85° to 120° C. SbF$_3$, 0.06 mole, SbCl$_5$, 0.0033 mole, and 1-bromo-2-dichloromethoxy-1,2,3,3-tetrafluorocyclopropane, 0.039 mole, are the reactants. A yield of 66% of the 1-bromo-2-difluoromethoxy product is obtained based on the starting dichloromethoxy analog. The purified product had a boiling point of 78° C, a density of ($d_4^{20}$) 1.852 and a refractive index ($n_D^{20}$) 1.3405.

EXAMPLE 6

1-Bromo-2-chlorofluoromethoxytetrafluorocyclopropane

Again the procedure of Example 2 can be used with a few changes in conditions and reactants. For the present illustrative purpose, the product was isolated from the preparation in Example 5 in yield of 22%, based on the starting dichloromethoxy analog. The chlorofluoromethoxy compound had a boiling point of 86° C, a density ($d_4^{20}$) of 1.85 and a refractive index ($n_D^{20}$) of 1.356.

EXAMPLE 7 to 10

The physiological effects of the cyclopropyl ethers prepared in the preceding examples were demonstrated as follows, using a standard test for evaluation of inhalation anesthetics similar to that described in Robbins [J. Pharmacology and Experimental Therapeutics 86, 197 (1946)].

Mice were exposed to the anesthetic for a period of 10 minutes in a rotating drum. Observations were then made of the pinch reflex, the corneal reflex and the return of the righting reflex. At least four graded doses were employed to determine the minimum concentration required to anesthetize 50% of the mice used ($AC_{50}$) and the minimum concentration required to kill 50% of the mice ($LC_{50}$). The anesthetic index (AI) was The compounds of this invention are therefore capable of inducing a state of anesthesia in air-breathing mammals, from which the latter recover, provided that the lethal concentration of anesthetic vapors is not reached. The compounds can be stored in containers of the type commonly used for conventional anesthetics of comparable boiling point, e.g. halothane, and they may be used in admixture with pharmaceutically acceptable diluents and stabilizers such as thymol, or in combination with one or more of the known inhalation anesthetics, such as nitrous oxide, ether, halothane, chloroform, methoxyflurane, and the like. In short, it should be understood that variations can be carried out in either the preparation or the administration of these compounds depending on factors such as economic considerations, level and duration of anesthesia desired, subject treated, and the like.

What is claimed is:

1. The process of inducing anesthesia in a mammal, which comprises administering by inhalation to said mammal an effective quantity, for inducing anesthesia, of a cycloporopyl ether selected from the group consisting of: 1-chloro-2-chlorofluoromethoxy-1,2,3,3-tetrafluorocyclopropane, 1-chloro-2-difluoromethoxy-1,2,3,3-tetrafluorocyclopropane, 1-bromo-2-chlorofluoromethoxy-1,2,3,3-tetrafluorocyclopropane and 1-bromo-2-difluoromethoxy-1,2,3,3-tetrafluorocyclopropane. clopropane.

2. The process of claim 1 wherein the ether administered is 1-chloro-2-chlorofluoromethoxy-1,2,3,3-tetrafluorocyclopropane.

3. The process of claim 1 wherein the ether administered is 1-chloro-2-difluoromethoxy-1,2,3,3-tetrafluorocyclopropane.

4. The process of claim 1 wherein the ether administered is 1-bromo-2-chlorofluoromethoxy-1,2,3,3-tetrafluorocyclopropane.

5. The process of claim 1 wherein the ether administered is 1-bromo-2-difluoromethoxy-1,2,3,3-tetrafluorocyclopropane.

* * * * *